US012193915B2

(12) United States Patent
Juaire

(10) Patent No.: US 12,193,915 B2
(45) Date of Patent: Jan. 14, 2025

(54) APPARATUS, SYSTEM, AND METHOD FOR AT LEAST ONE OF ICING, HEATING, AND COMPRESSING A USER'S BODY PART

(71) Applicant: Stephen Eugene Juaire, West Elbow Drive, FL (US)

(72) Inventor: Stephen Eugene Juaire, West Elbow Drive, FL (US)

( * ) Notice: Subject to any disclaimer, the term of this patent is extended or adjusted under 35 U.S.C. 154(b) by 113 days.

(21) Appl. No.: 18/130,766

(22) Filed: Apr. 4, 2023

(65) Prior Publication Data
US 2023/0233379 A1    Jul. 27, 2023

Related U.S. Application Data

(63) Continuation-in-part of application No. 17/941,511, filed on Sep. 9, 2022, now Pat. No. 11,638,468.

(60) Provisional application No. 63/242,398, filed on Sep. 9, 2021.

(51) Int. Cl.
| *A61F 5/01* | (2006.01) |
| *A61F 7/08* | (2006.01) |
| *A61F 7/10* | (2006.01) |
| *A61F 13/01* | (2024.01) |
| *A61F 13/00* | (2006.01) |

(52) U.S. Cl.
CPC ........ *A61F 13/01038* (2024.01); *A61F 7/086* (2013.01); *A61F 7/103* (2013.01); *A61F 2007/105* (2013.01); *A61F 2013/00131* (2013.01); *A61F 2013/0028* (2013.01)

(58) Field of Classification Search
CPC .... A61F 13/01038; A61F 7/086; A61F 7/103; A61F 2007/105; A61F 2013/00131; A61F 2013/0028
See application file for complete search history.

(56) References Cited

U.S. PATENT DOCUMENTS

| 932,177 | A | * | 8/1909 | Roth | A61F 5/0111 |
| | | | | | 602/23 |
| 1,354,260 | A | * | 9/1920 | Clara | A44B 11/25 |
| | | | | | 24/578.15 |
| 3,678,936 | A | * | 7/1972 | McCormick | A61F 7/103 |
| | | | | | 607/112 |

(Continued)

FOREIGN PATENT DOCUMENTS

CN    116849500 A  * 10/2023  ............. A47G 19/16

*Primary Examiner* — Jason W San
(74) *Attorney, Agent, or Firm* — Derek Fahey, Esq.; The Plus IP Firm, PLLC

(57) ABSTRACT

A wearable device for at least one of icing, heating and compressing a user's body part is disclosed. The wearable device comprises an inner part and an outer part. The outer part is arranged with the inner part such that the outer part surrounds the inner part. A compartment is defined by the space between the outer part and the inner part and above the first attaching means. A compression force is provided by the second set of elastic properties compressing at least one of the hot element and the cold element against the user's body part thereby eliminating a second attaching means above the first attaching means within the compartment. At least one handle is in attachment with the outer part. The wearable device further comprises at least one band disposed on the outer part between the outer part upper end and outer part lower end.

20 Claims, 12 Drawing Sheets

(56) References Cited

U.S. PATENT DOCUMENTS

| | | | | |
|---|---|---|---|---|
| 4,356,709 A * | 11/1982 | Alexander | A42B 1/008 | 62/259.3 |
| 4,527,566 A * | 7/1985 | Abare | A61F 7/02 | D24/206 |
| 4,676,247 A * | 6/1987 | Van Cleve | A61F 7/02 | 62/530 |
| 4,688,572 A * | 8/1987 | Hubbard | A61F 7/02 | D24/207 |
| 4,926,851 A * | 5/1990 | Bulley | D04B 1/18 | 602/76 |
| 4,955,369 A * | 9/1990 | Bledsoe | A61F 5/0123 | 602/26 |
| 5,005,374 A * | 4/1991 | Spitler | F25D 3/08 | 383/110 |
| 5,038,779 A * | 8/1991 | Barry | A41D 13/0058 | 607/108 |
| 5,072,455 A * | 12/1991 | St. Ours | A41D 13/0058 | 2/92 |
| 5,119,513 A * | 6/1992 | McKay | A41D 20/005 | 2/DIG. 11 |
| 5,154,690 A * | 10/1992 | Shiono | A61F 5/0102 | 602/61 |
| 5,288,287 A * | 2/1994 | Castillo | A61F 5/0123 | 602/26 |
| 5,305,470 A * | 4/1994 | McKay | A41D 20/005 | 2/171.2 |
| 5,383,845 A * | 1/1995 | Nebolon | A61F 5/0125 | 602/26 |
| 5,387,185 A * | 2/1995 | Johnson, Jr. | A61F 5/0585 | 602/5 |
| 5,407,421 A * | 4/1995 | Goldsmith | A61F 7/02 | 602/5 |
| 5,415,624 A * | 5/1995 | Williams | A61F 7/02 | 602/14 |
| 5,425,702 A * | 6/1995 | Carn | A61F 13/00059 | 602/76 |
| 5,458,565 A * | 10/1995 | Tillinghast, III | A61F 5/0123 | 602/26 |
| 5,716,388 A * | 2/1998 | Petelle | A61F 7/02 | 607/108 |
| 5,826,273 A * | 10/1998 | Eckes | A41D 13/0051 | 2/69 |
| 5,918,310 A * | 7/1999 | Farahany | A41D 13/0158 | 2/455 |
| 5,971,947 A * | 10/1999 | McNally | A61F 13/108 | 602/14 |
| 6,014,771 A * | 1/2000 | Kirven | A41D 13/015 | 2/24 |
| 6,582,383 B2 * | 6/2003 | Horning | A61F 7/10 | 607/114 |
| 6,585,673 B1 * | 7/2003 | Bass | A61F 7/02 | 602/61 |
| 6,972,029 B2 * | 12/2005 | Mayrhofer | A61F 7/02 | 607/108 |
| 7,060,086 B2 * | 6/2006 | Wilson | A61F 7/02 | 602/61 |
| 7,309,275 B1 * | 12/2007 | Morales | A41C 3/04 | 450/38 |
| 7,507,215 B2 * | 3/2009 | Ryan | A61F 5/0123 | 602/26 |
| 7,621,944 B2 * | 11/2009 | Wilson | A61F 7/02 | 607/108 |
| 7,704,218 B2 * | 4/2010 | Einarsson | A61F 5/0125 | 602/5 |
| 7,739,748 B2 * | 6/2010 | Nilforushan | A41D 13/005 | 2/268 |
| 7,959,588 B1 * | 6/2011 | Wolpa | A61F 5/012 | 602/61 |
| 8,118,762 B2 * | 2/2012 | Bort | A61F 13/062 | 602/61 |
| 8,256,034 B2 * | 9/2012 | Berner, Jr. | A41D 31/185 | 2/455 |
| 8,740,829 B2 * | 6/2014 | Lee | F16B 21/09 | 602/26 |
| 8,876,875 B1 * | 11/2014 | Nilforushan | A61H 1/008 | 607/108 |
| 9,017,274 B2 * | 4/2015 | Forbes | A61F 5/0109 | 602/26 |
| 9,956,113 B2 * | 5/2018 | Santa Maria | A61H 9/0078 | |
| 10,314,351 B2 * | 6/2019 | Stevenson | A41D 20/005 | |
| 2001/0037076 A1 * | 11/2001 | Shelton | A41D 13/0058 | 602/5 |
| 2002/0052568 A1 * | 5/2002 | Houser | B60R 22/001 | 602/26 |
| 2003/0055366 A1 * | 3/2003 | Chalek | A61F 7/02 | 602/2 |
| 2003/0221241 A1 * | 12/2003 | Rivera | A41D 20/005 | 2/170 |
| 2007/0107456 A1 * | 5/2007 | Yeager | A41D 13/0053 | 62/331 |
| 2008/0040831 A1 * | 2/2008 | Nilforushan | A61F 7/02 | 219/211 |
| 2008/0125842 A1 * | 5/2008 | Petitt | A61F 7/02 | 607/108 |
| 2008/0222766 A1 * | 9/2008 | Arensdorf | A63B 71/08 | 2/22 |
| 2009/0000002 A1 * | 1/2009 | Hadash | A41D 13/0058 | 2/247 |
| 2009/0125086 A1 * | 5/2009 | Juta | A61F 7/03 | 607/108 |
| 2009/0306749 A1 * | 12/2009 | Mulindwa | A61F 7/08 | 607/108 |
| 2010/0059559 A1 * | 3/2010 | Given | A45F 5/00 | 224/267 |
| 2010/0100019 A1 * | 4/2010 | Chen | A61F 5/03 | 602/5 |
| 2010/0331750 A1 * | 12/2010 | Ingimundarson | A61F 5/0102 | 602/26 |
| 2010/0331752 A1 * | 12/2010 | Cumming | A61F 13/12 | 607/114 |
| 2011/0040227 A1 * | 2/2011 | Magri | A61F 13/10 | 602/62 |
| 2011/0041839 A1 * | 2/2011 | Lee | A61F 5/30 | 128/109.1 |
| 2011/0082403 A1 * | 4/2011 | Hill | A61F 5/0113 | 602/28 |
| 2011/0137221 A1 * | 6/2011 | Brown | A61F 5/0106 | 602/26 |
| 2011/0196458 A1 * | 8/2011 | Bratcher, Jr. | A61F 7/02 | 607/108 |
| 2012/0010545 A1 * | 1/2012 | McSpadden | A61F 5/0123 | 602/2 |
| 2012/0078147 A1 * | 3/2012 | Ogulnick | A61F 13/06 | 602/2 |
| 2012/0160229 A1 * | 6/2012 | Tieu | F24V 30/00 | 126/204 |
| 2012/0165713 A1 * | 6/2012 | Forbes | A61F 5/0109 | 602/26 |
| 2012/0296252 A1 * | 11/2012 | Cumming | A61F 13/12 | 602/53 |
| 2013/0012760 A1 * | 1/2013 | Tripolsky | A61N 2/06 | 600/15 |
| 2013/0150761 A1 * | 6/2013 | Romo | A61F 5/0123 | 602/16 |
| 2014/0088478 A1 * | 3/2014 | Bue, Jr. | A61H 1/006 | 602/26 |
| 2014/0123440 A1 * | 5/2014 | Capra | A61F 5/01 | 29/3 |
| 2014/0303534 A1 * | 10/2014 | Huffa | A61F 5/0123 | 602/6 |
| 2014/0330184 A1 * | 11/2014 | Kilbey | A61F 5/0106 | 602/2 |
| 2014/0336544 A1 * | 11/2014 | Ransom | A61F 7/02 | 601/18 |
| 2015/0073326 A1 * | 3/2015 | Shih | A61F 7/10 | 602/53 |
| 2016/0008157 A1 * | 1/2016 | Brookover | A61F 5/0125 | 602/26 |

(56) References Cited

U.S. PATENT DOCUMENTS

| | | | |
|---|---|---|---|
| 2016/0120237 A1* | 5/2016 | Isanhart | D01F 6/90 2/253 |
| 2016/0120691 A1* | 5/2016 | Kirwan | A61F 7/02 607/111 |
| 2016/0143772 A1* | 5/2016 | McLain | A61F 7/02 602/2 |
| 2016/0228288 A1* | 8/2016 | Nelson | A61F 13/143 |
| 2017/0020720 A1* | 1/2017 | O'Neal | A61F 7/02 |
| 2017/0027734 A1* | 2/2017 | Riordan | A61F 7/02 |
| 2017/0231796 A1* | 8/2017 | Romo | A61F 5/0195 602/16 |
| 2017/0340469 A1* | 11/2017 | Huffa | A61F 5/0102 |
| 2017/0347742 A1* | 12/2017 | Turner | A41D 13/0587 |
| 2018/0049913 A1* | 2/2018 | Spears | A61F 7/10 |
| 2018/0078398 A1* | 3/2018 | Ingimundarson | A61F 5/34 |
| 2019/0142620 A1* | 5/2019 | Omarsson | A61F 5/0109 602/5 |
| 2019/0282407 A1* | 9/2019 | Davis | A61F 7/02 |
| 2020/0405531 A1* | 12/2020 | Juaire | A41D 1/06 |
| 2020/0405533 A1* | 12/2020 | Check | A61F 7/10 |

\* cited by examiner

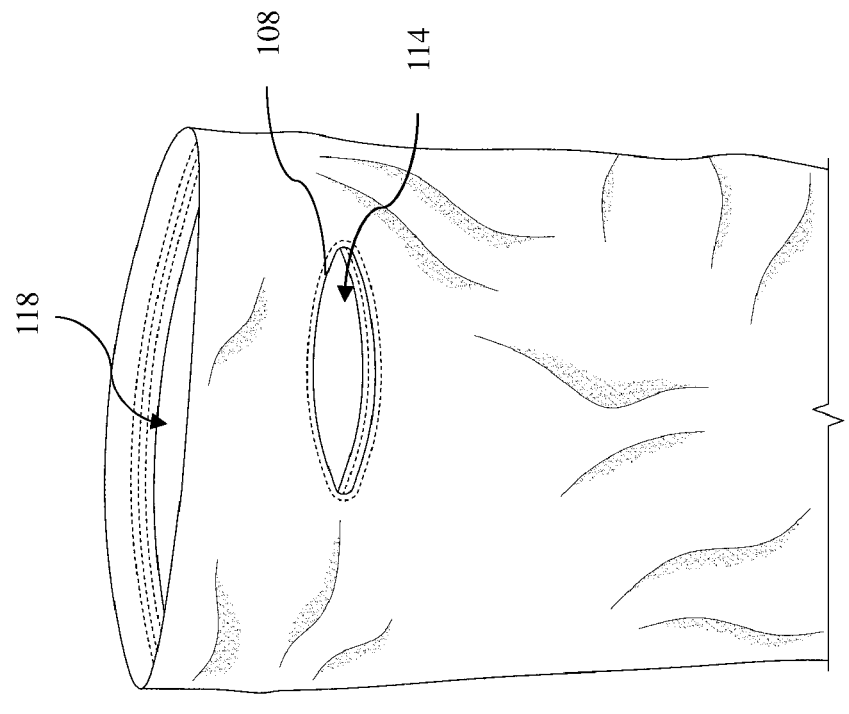
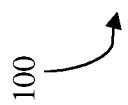
FIG. 1A

APPARATUS, SYSTEM, AND METHOD FOR AT LEAST ONE OF ICING, HEATING, AND COMPRESSING A USER'S BODY PART

CROSS-REFERENCE TO RELATED APPLICATIONS

This is a continuation in part application that claims priority to U.S. Non-Provisional application Ser. No. 17/941,511 titled "APPARATUS, SYSTEM, AND METHOD FOR AT LEAST ONE OF ICING, HEATING, AND COMPRESSING A USER'S BODY PART" and filed Sep. 9, 2022, which claims priority to U.S. Provisional Application Ser. No. 63/242,398 titled "APPARATUS, SYSTEM, AND METHOD FOR AT LEAST ONE OF ICING, HEATING, AND COMPRESSING A USER'S BODY PART" and filed Sep. 9, 2021, and the subject matter both of which is incorporated herein by reference.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISC

Not applicable.

TECHNICAL FIELD

The present disclosure relates to the field of therapeutic modalities, and more specifically to wearable temperature and compression therapy devices for relieving pain and promoting healing of everyday aches and injuries.

BACKGROUND

Cold therapy and heat therapy are useful adjuncts for the treatment of musculoskeletal injuries and soft tissue injuries. The goal of cold and heat therapy is to alter tissue temperature in a targeted region over time for the purpose of inducing a desired biological response. Static compression is often used in conjunction with cold and heat therapy for the care of acute injuries. To date, the primary reason for using compression is to increase external pressure on the tissue to prevent edema formation. This occurs by hindering fluid loss from the vessels in the injured area, making it more difficult for fluids to accumulate.

Cold therapy, also known as cryotherapy, is the application of any substance or physical medium to the body that removes heat, decreasing the temperature of the contact area and adjacent tissues. Cold therapy has multiple physiological effects on injured tissue. Decreasing temperatures of skin and muscle reduces blood flow to the cooled tissues by activating a sympathetic vasoconstrictive reflex. Cold-induced decreases in blood flow reduce edema and slow the delivery of inflammatory mediators, reducing inflammation of the affected area. Decreasing tissue temperature also reduces the metabolic demand of hypoxic tissues, potentially preventing secondary hypoxic damage in injured tissue. Many devices are available for application of cold therapy, including bags of crushed ice, and commercially available ice and gel packs.

Heat therapy, also known as thermotherapy, is the application of heat to the body resulting in increased tissue temperature. Heat therapy has multiple physiological effects on injured tissue. Rising temperatures of skin and muscle produce vasodilation that increases the supply of oxygen and nutrients and the elimination of carbon dioxide and metabolic waste. Additional physiological effects of heat therapy include increasing the extensibility of collagen tissues, decreasing joint stiffness, reducing pain, relieving muscle spasms, reducing inflammation, edema, and aids in the post-acute phase of healing. Superficial modes of heat therapy include hot water bottles, heat pads, and heated stones.

Traditional cold and heat therapy modalities can provide meaningful therapy but are often plagued by several challenges such as providing relief to only a specific area of the body. Individuals often need to simultaneously treat more than one soft tissue area within close proximity. For example, an injury to a hamstring area or group of muscles often includes the semimembranosus, semitendinosus, biceps femoris, quadratus femoris, and iliotibial band. As a result, the individual cannot treat the entirety of the injured area because the damaged soft tissue extends beyond the specific area covered by the therapeutic modality.

Moreover, individuals have a difficult time applying and maintaining therapeutic modalities in the desired position. For example, ice packs rarely stay in place due to their unconventional shape, and plastic bags of ice tend to leak and wet clothing. Additionally, compression is difficult to apply over therapeutic modalities. Therapeutic modalities require a protective layer of material to prevent the therapeutic modality from directly touching the skin and causing skin contact burns.

Therefore, a need exists to improve over the prior art and more particularly, for a therapeutic cold and heat delivery device that provides uniform pressure and temperature to an unrestricted combination of soft tissue groupings in the human body.

SUMMARY

An apparatus, system, and method for a wearable device for at least one of icing, heating and compressing a user's body part is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a system for at least one of icing, heating and compressing a user's body part is disclosed. The system comprises an inner part having an inner part upper end and an inner part lower end defining an inner part length, wherein the inner part has a first set of elastic properties and a first tubular shape such that the inner part is configured to fit snugly around a user's body part, and wherein the inner part has an inner part thickness. The system also comprises an outer part having an outer part upper end and an outer part lower end defining an outer part length, wherein the outer part has a second set of elastic properties and a second tubular shape. The outer part is arranged with the inner part such that the outer part surrounds the inner part. The outer part has an outer part thickness that is greater than the inner part thickness. The system further comprises a first attaching means for attaching the inner part lower end to the outer part lower end. A compartment is defined by the space between the outer part and the inner part and above the first attaching means. A compression force is provided by the second set of elastic properties compressing at least one of the hot element and the cold element against the user's body part thereby eliminating a second attaching means, being structure, above the first attaching means within the compartment. The second attaching means being structure other than the outer part for securing the at least one of the hot element and cold element against the user's body part. At least one handle is in attachment with the outer part. The at least one handle is defined by a first handle opening extending through the outer part and the inner part. The system further comprises at least one band disposed on the outer part between the outer part upper end and outer part lower end. The band has a third set of elastic properties that is greater than the first set of elastic properties and the second set of elastic properties. The first set of elastic properties defines a first resilient force of between 17 mmHg-22 mmHg. The second set of elastic properties defines a second resilient force of between 17 mmHg-22 mmHg. The compression force is providing an inward force of at least 17 mmHg against the user's body part. The first attaching means comprises stitching attaching the inner part lower end to the outer part lower end. The second attaching means comprises a strap, button, pocket, hook and look fastener, snap, ridge or any combination thereof.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIG. 1A is a side perspective side view of an apparatus for at least one of icing, heating and compressing a user's body part, according to an example embodiment;

DETAILED DESCRIPTION

Figure 1B:
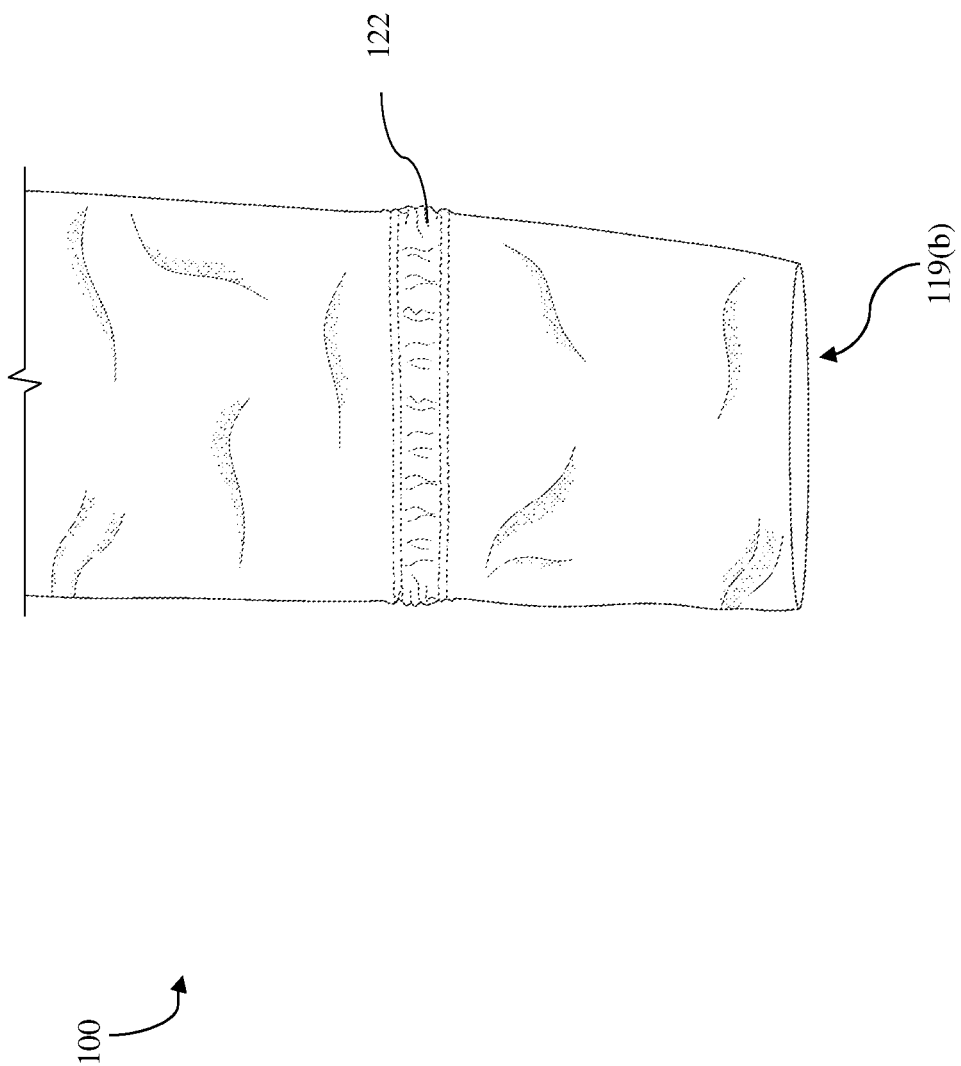
FIG. 1B is a side perspective side view of an apparatus for at least one of icing, heating and compressing a user's body part, according to an example embodiment.
Figure 2:
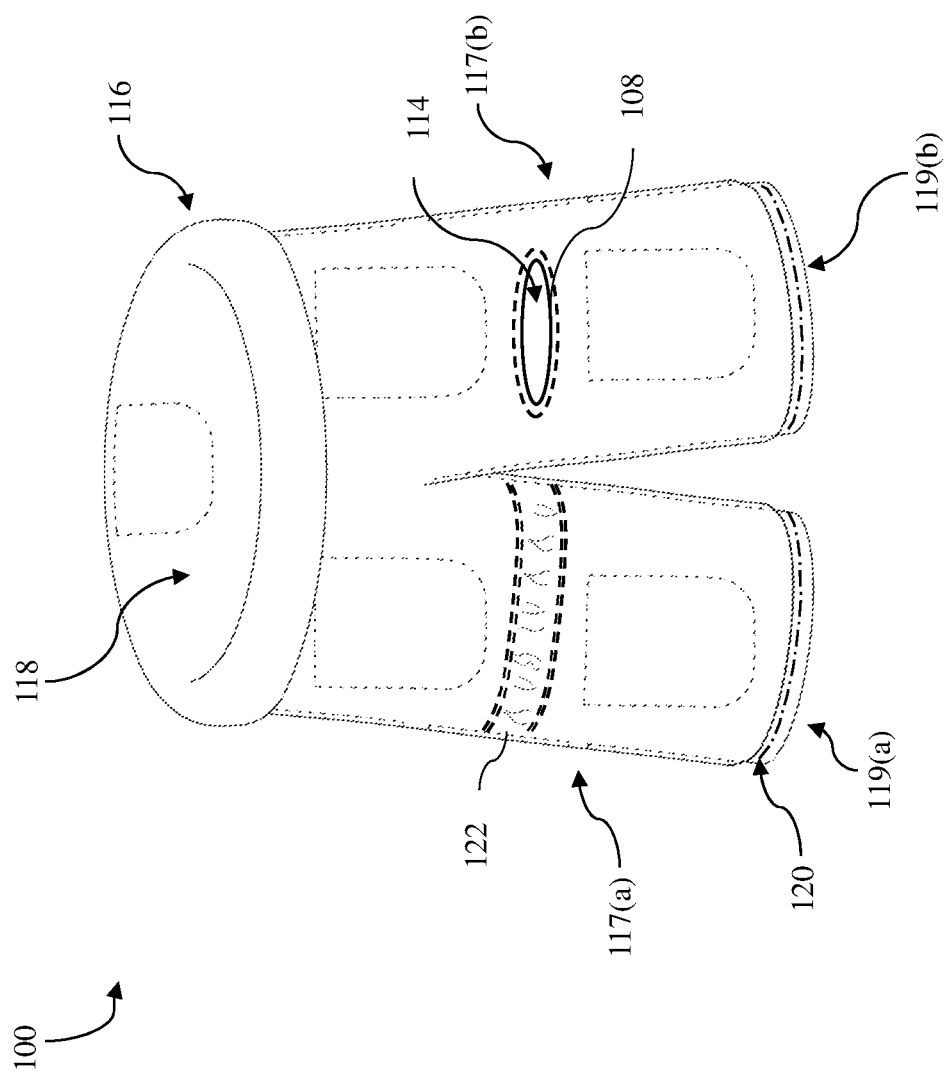
FIG. 2 is a front perspective side view of an apparatus for at least one of icing, heating and compressing a user's body part, according to an example embodiment.

The following detailed description refers to the accompanying drawings. Whenever possible, the same reference numbers are used in the drawings and the following description to refer to the same or similar elements. The figures are drawn to scale. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by providing uniform pressure and temperature to an unrestricted combination of soft tissue groupings in the human body. In other words, a therapeutic modality is not restricted to a particular location or region on a user's body. The wearable device includes a compartment positioned outward from the user's body for receiving ice defined by a space between an outer part and an inner part of the wearable device. The space may vary in size. A compression force is provided by a second set of elastic properties compressing and receiving at least one of a hot element and a cold element against the user's body part thereby eliminating a second attaching means such as a strap, button, pocket, hook and loop fastener, ridge or any combination thereof. The wearable device also includes handles configured to help the user pull the wearable device onto the user's body part and bands configured to provide more compression to target areas of the user's body part. The handles provide an easier means of positioning the wearable device on the user's body part. The bands tighten the wearable device proximate to the target areas of the user's body part to prevent at least one of the hot element or the cold element from moving out of position and to stabilize the muscles near the target area. Proximate may be defined as close to or near. As a result, the unrestricted application of a therapeutic modality provides a more effective treatment method because the wearable device conforms to the body and anchors the therapeutic modality precisely over the injury.

Referring now to the Figures, FIGS. 1A-6 illustrate an apparatus and system for at least one of icing, heating, and compressing a user's body part 101, and will be discussed together for ease of reference. The wearable device 100 comprises an inner part 105 and outer part 110. The outer part 110 is arranged with the inner part 105 such that the outer part surrounds the inner part. The inner part 105 includes an inner part upper end 106 and an inner part lower end 107, defining an inner part length. The inner part provides a protective insulation layer between a cold or heat modality and a user's skin. The inner part 105 has a first set of elastic properties and a first tubular shape such that the inner part 105 is configured to fit snugly around a user's body part. The inner part also has an inner part thickness configured to allow the inner part to exchange heat with the user's body part. The purpose of the inner part is to protect the user's skin from at least of the hot element and the cold element when the wearable device is worn. The inner part thickness is configured to allow the hot element or cold element to warm or cool the target area of the user's body part while also preventing the hot element or cold element from directly contacting the user's skin. The outer part 110 includes an outer part upper end 111 and an outer part lower end 112 defining an outer part length. The outer part is comprised of a water-wicking material to draw moisture away from the body and prevent ice from leaking during treatment. The outer part 110 has a second set of elastic properties and a second tubular shape. The first set of elastic properties defines a first resilient force of between 17 mmHg-22 mmHg, and as described more fully below, when the wearable device 100 is in a fully sealed configuration, the second set of elastic properties defines a second resilient force of between 17 mmHg-22 mmHg. Elastic compression is the resilient force exerted by the wearable device on the user's body part. Compression is expressed in millimeters of mercury (mmHg). A higher number is correlated with a higher amount of compression while a lower number correlates with a lower compression.

At least one handle 108 is in attachment with the outer part to allow the user to pull up the wearable device when being worn. The at least one handle is defined by a first handle opening 114 extending through the outer part and the inner part. The handle allows provides a convenient means for the user to pull up the wearable device such that wearable device may be easily positioned on the user's body part. The handle is sized such that the user can grasp the handle with its entire hand. Additionally, because the wearable device may be tight on the user, the handles provide the user with a reliable means of grasping the wearable device to easily pull up the wearable device on the user's body part. In some embodiments. At least one handle may be disposed on opposing sides of the wearable device such that the user may pull up the wearable device evenly using two hands. In other embodiments, the handles may be positioned on any portion of the wearable device allowing the user to pull up the wearable device.

At least one band 122, as shown in FIG. 1B, is disposed on the outer part between the outer part upper end and outer part lower end. The band is looped around the wearable device such that the band is around the body part. The band is in attachment with the outer part but is outside the inner surface of the outer part. For example, the band may be sewn or embedded into the outer part such that the band is not inside the gap between the outer part and the inner part. This prevents the band from obstructing the compartment. The band has a third set of elastic properties that is greater than the first set of elastic properties and the second set of elastic properties. The third set of elastic properties has a third resilient force that is greater than the first resilient force and the second resilient force. The band causes the wearable device to be tighter around the target area of user's body part, where the band is proximate to. The target area may be where therapeutic modalities are positioned. For example, the target area may be where the user requires at least one of the hot element or the cold element. The tightness of the band prevents the hot element or cold element from sliding down and away from the target area. The target area may also be where the user requires more compression. The increased compression helps stabilize the muscles near the target area of the user's body part to help decrease fatigue and/or decrease soreness.

In the present embodiment, the wearable device of the system is a pair of shorts comprising a main body member 116 and a pair of leg sections 117 (a), 117 (b). The main body member is generally tubular for encircling the hip region of a user. The upper end of the main body member has an opening 118 to accommodate the hip region of a user. The main body member opening is defined by a flap 150 forming a seal at the upper end of the wearable device 100. The flap is defined by the inner part length being greater than the outer part length such that the inner part upper end 106 folds over the outer part upper end 111. When the wearable device 100 is in a fully sealed configuration, the flap 150 extends at least 1.0 inch from a top edge of the upper end of the outer part. The flap prevents water or perspiration from the heat element to escape the upper end of the main body. The lower end of the main body member has a pair of openings 119 (a), 119 (b) to accommodate the legs of the user and are appropriately sized and positioned so that the legs of the user may comfortably extend through the main body member.

The wearable device may be comprised of different flexible materials such as Lycra, polyester, cotton blend, nylon, similar blends, or any other suitable materials known in the art. More specifically, and without limitation, the material can be moisture absorbent, breathable, stretchable, meshed, or any blend or combination thereof. The material can also be thermoconductive to conduct heat better, or thermoreflective to help keep heat inside the wearable device. Further, the thickness and elasticity of fabric may be varied to accommodate different users and conditions. It should be appreciated that the wearable device can have other shapes and dimensions to accommodate men, women, and children of all sizes, and such variations are within the spirit and scope of the claimed invention.

The wearable device further includes a first attaching means 120 for attaching the inner part lower end 107 to the outer part lower end 112. The first attaching means is configured such that the therapeutic modality does not move below the lower ends. In the present embodiment, the first attaching means 120 comprises stitching the inner part lower end 107 to the outer part lower end 112. A plurality of different stitch patterns can be used including a chain stitch, straight stitch, and zigzag stitch, and such variations are within the spirit and scope of the claimed invention. Additionally, the stitching thread can be comprised of a natural fiber (cotton, wool, silk, linen) or a synthetic fiber (rayon, polyester, nylon). It should also be appreciated that other attachment means can be used to attach the inner part lower end 107 to the outer part lower end 112, including fasteners, snaps, zippers, ties, or any other suitable method known in the art.

Figure 6:
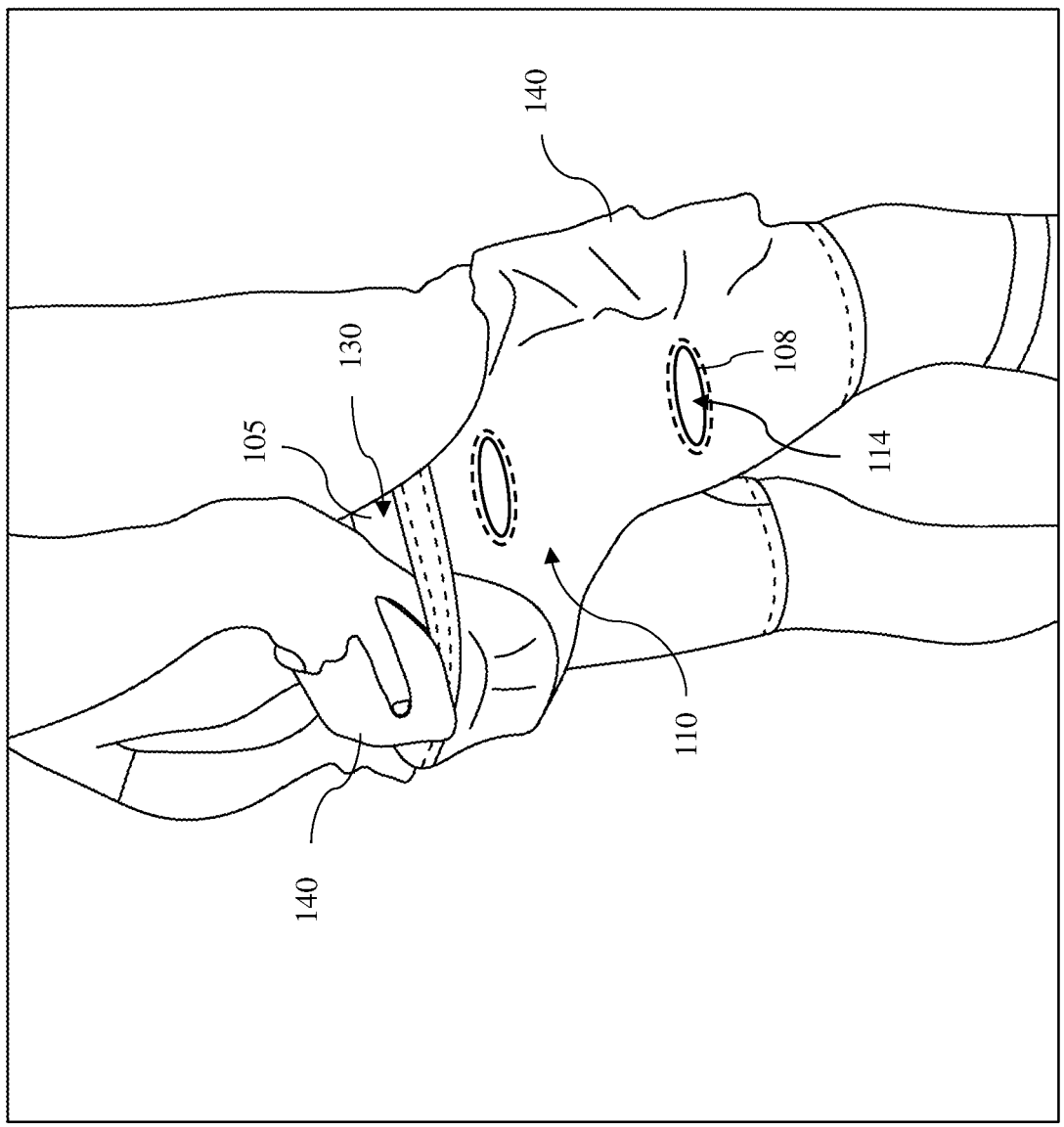
FIG. 6 is a side perspective view of an apparatus for at least one of icing, heating and compressing a user's body part, wherein a user is positioning a cold or hot element within the compartment, according to an example embodiment.

The wearable device further includes a compartment 130 defined by the space between the outer part 110 and the inner part 105, located above the first attaching means 120. It is understood that when the wearable device is worn by the user the inner part and the outer "sandwich" the cold element or hot element that has been inserted in the compartment. The inner layer may also provide an increased amount of friction to further prevent the cold or hot element from moving and facilitates maintaining the cold or hot element in a single position between the inner layer and outer layer unless acted on by a force greater than the inward compression force. The compartment is configured for receiving at least one of a hot element and cold element 140. The present invention improves upon the prior art by allowing the unrestricted application of the therapeutic modality to the user's body. In other words, the therapeutic modality is not limited or restricted to a particular location or region on the user's body. As best shown in FIG. 6, when the wearable device 100 is not in a fully sealed configuration, the therapeutic modality may be positioned and adjusted without removing, changing or adding layers within the compartment in an unlimited number of positions within the compartment spanning the entire wearable device. As a result, the unrestricted application of the therapeutic modality provides a more effective treatment method because the wearable device conforms to the body and anchors the therapeutic modality precisely over the injury.

Figure 3:
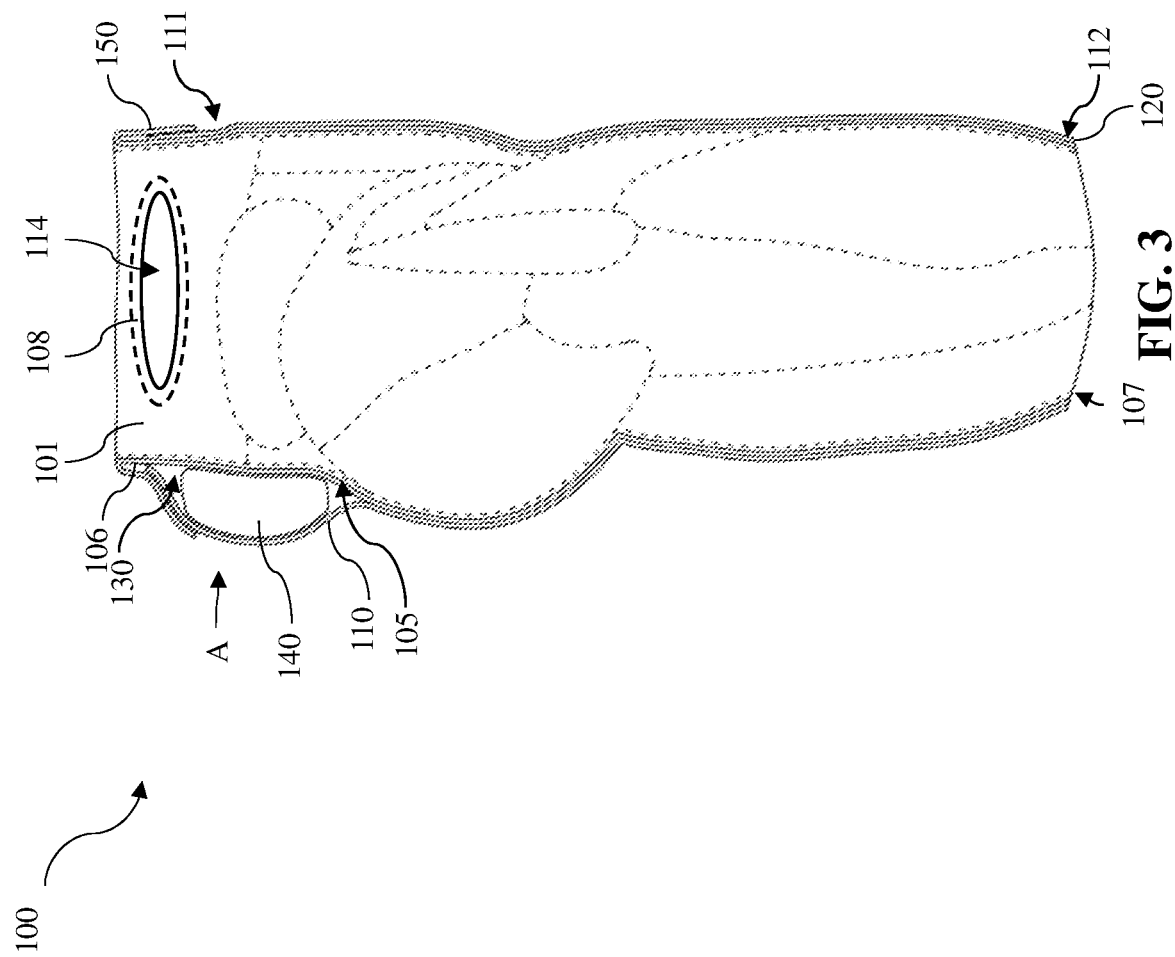
FIG. 3 is a side cross-sectional view of a system for at least one of icing, heating and compressing a user's body part, wherein a cold or hot element is located in a first area within the compartment, according to an example embodiment.
Figure 4:
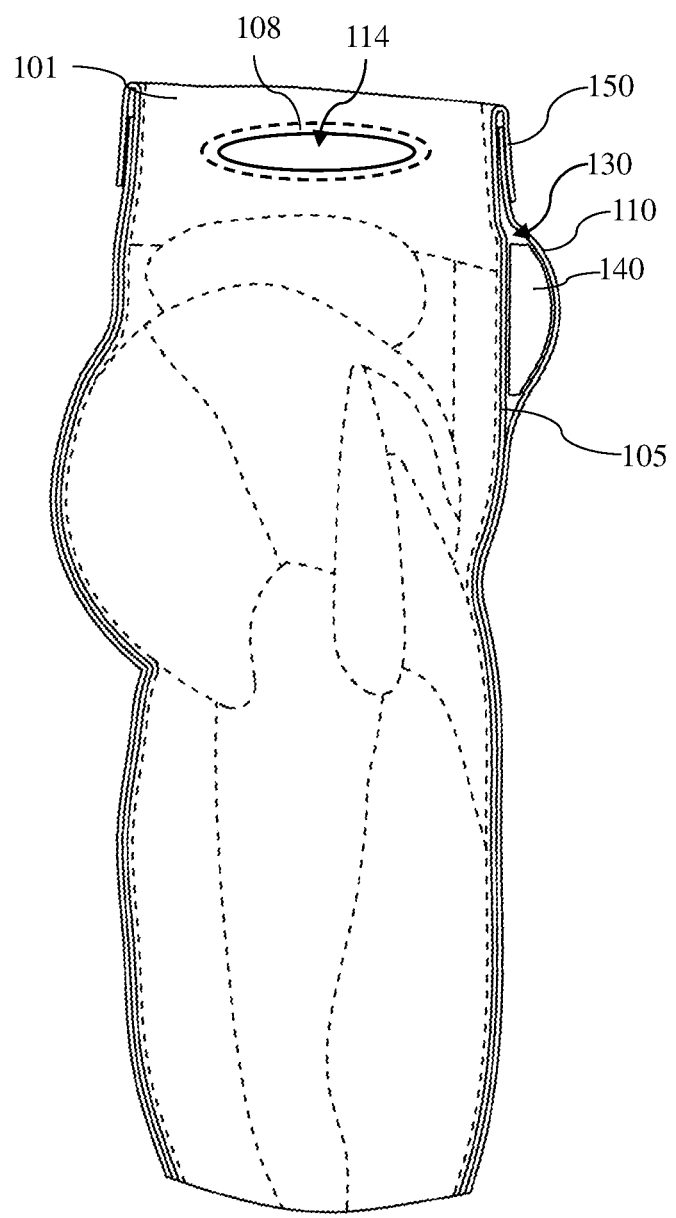
FIG. 4 is a side cross-sectional view of a system for at least one of icing, heating and compressing a user's body part, wherein a cold or hot element is located in a second area within the compartment, according to an example embodiment.
Figure 5:
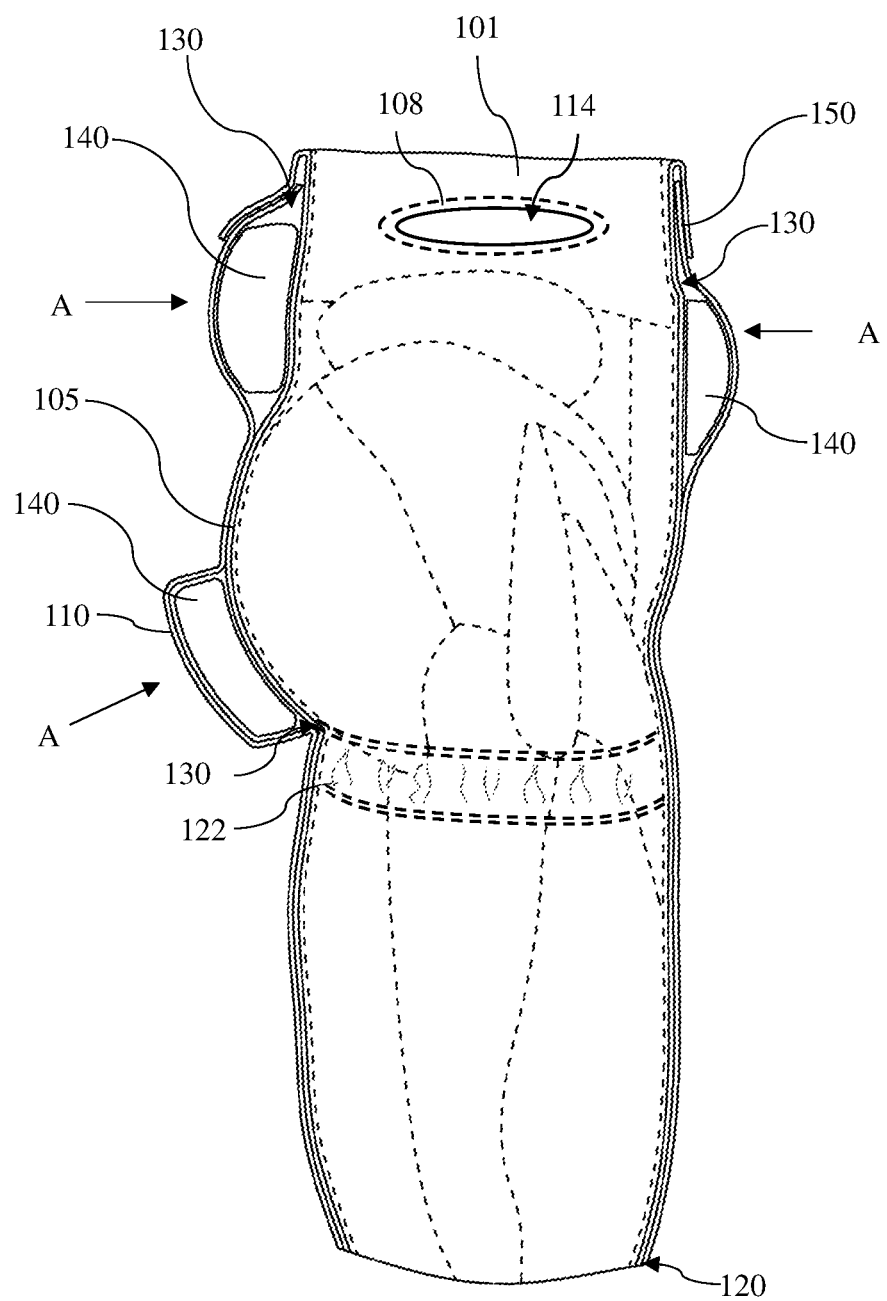
FIG. 5 is a side cross-sectional view of a system for at least one of icing, heating and compressing a user's body part, wherein a plurality of cold or hot elements are located in different areas within the compartment, according to an example embodiment.

A compression force is provided by the second set of elastic properties compressing and securing at least one of a hot element and cold element against the user's body part 101. A The hot and cold elements may be comprised of crushed ice, commercially available ice and gel packs, hot water bottles, heat pads, and heated stones. However, other devices or apparatus may be used for hot or cold elements that are within the spirit and scope of the present invention. The compression force provides an inward force (in the direction of line A) of at least 17 mmHg against the user's body part, thereby eliminating a second attaching means above the first attaching means 120. The second attaching means being a structure other than the outer part 110 for securing the at least one of the hot element and cold element against the user's body part 101, and may include a strap, button, pocket, hook and look fastener, snap, ridge or any combination thereof. In other words, the outer part having the second set of elastic properties eliminates the need for unnecessary pockets, straps of fasteners for securing the hot or cold element against the user's body. FIGS. 3-5 illustrates that the wearable device snugly fits the body of the user such that multiple therapeutic modalities located inside the compartment are anchored precisely over the desired area due to the snug fit of the wearable device. For example, in FIG. 3, a cold element 140 is positioned over the lower back (lumbar muscle) of the user 101, and in FIG. 4, a cold element positioned over the anterior wall (abdominal muscle) of the user 101. In FIG. 5, three cold elements are simultaneously positioned over the lower back (lumbar muscle), the anterior wall (abdominal muscle), and posterior pelvic region (gluteus maximus muscle) of the user 101. By eliminating a second attaching means, being structure, above the first attaching means, the wearable device can be worn as any layer of clothing, including as an undergarment or as an over-garment, and permits the user to move, in moderation, without disturbing the precision of treatment. Additionally, by eliminating the second attaching means allows the user to position the hot element or cold element in a much greater amount of locations more easily that the existing prior art.

Figure 7:
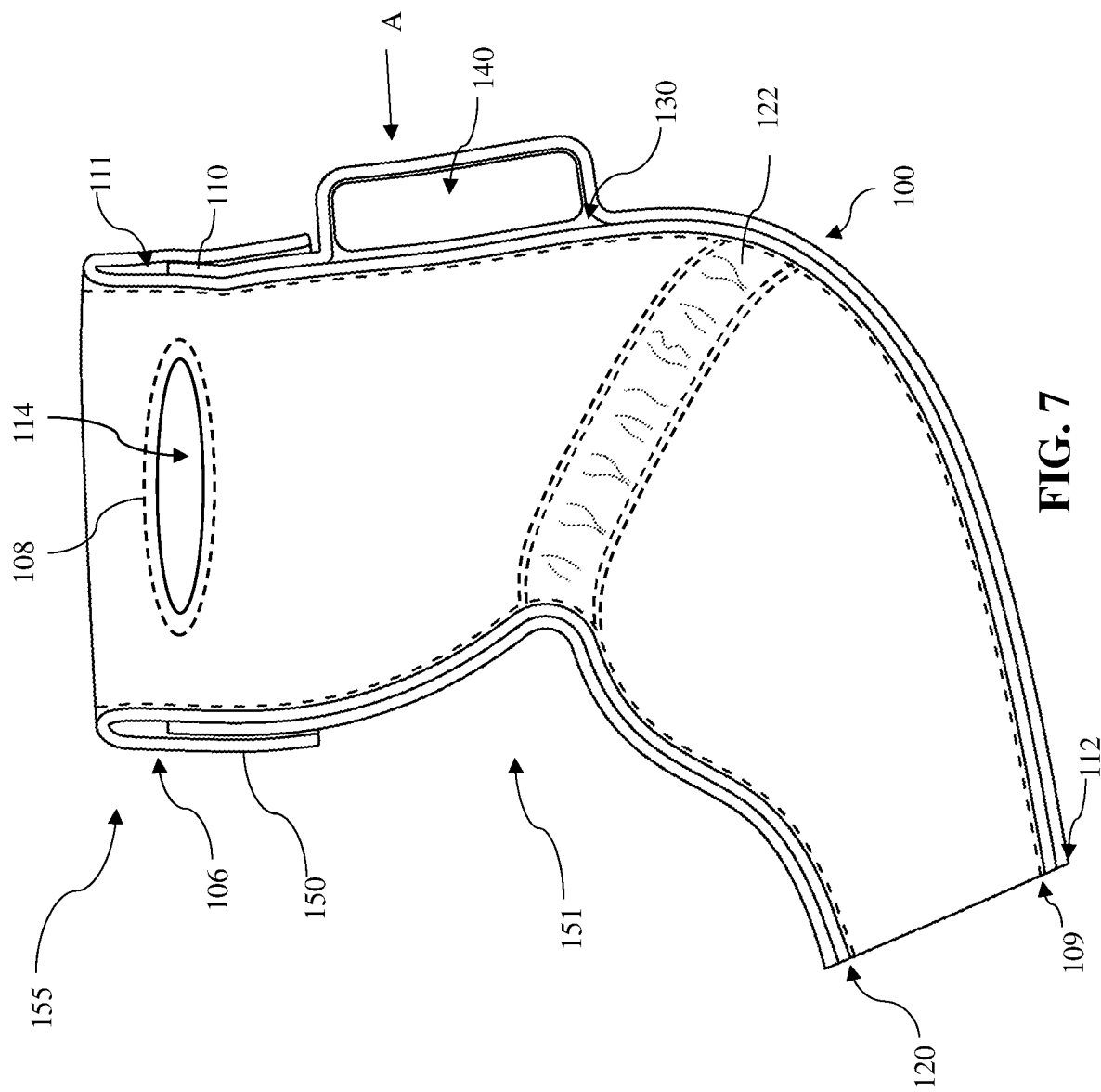
FIG. 7 is a side cross-sectional view of a system for at least one of icing, heating and compressing a user's body part, according to an example embodiment.
Figure 8:
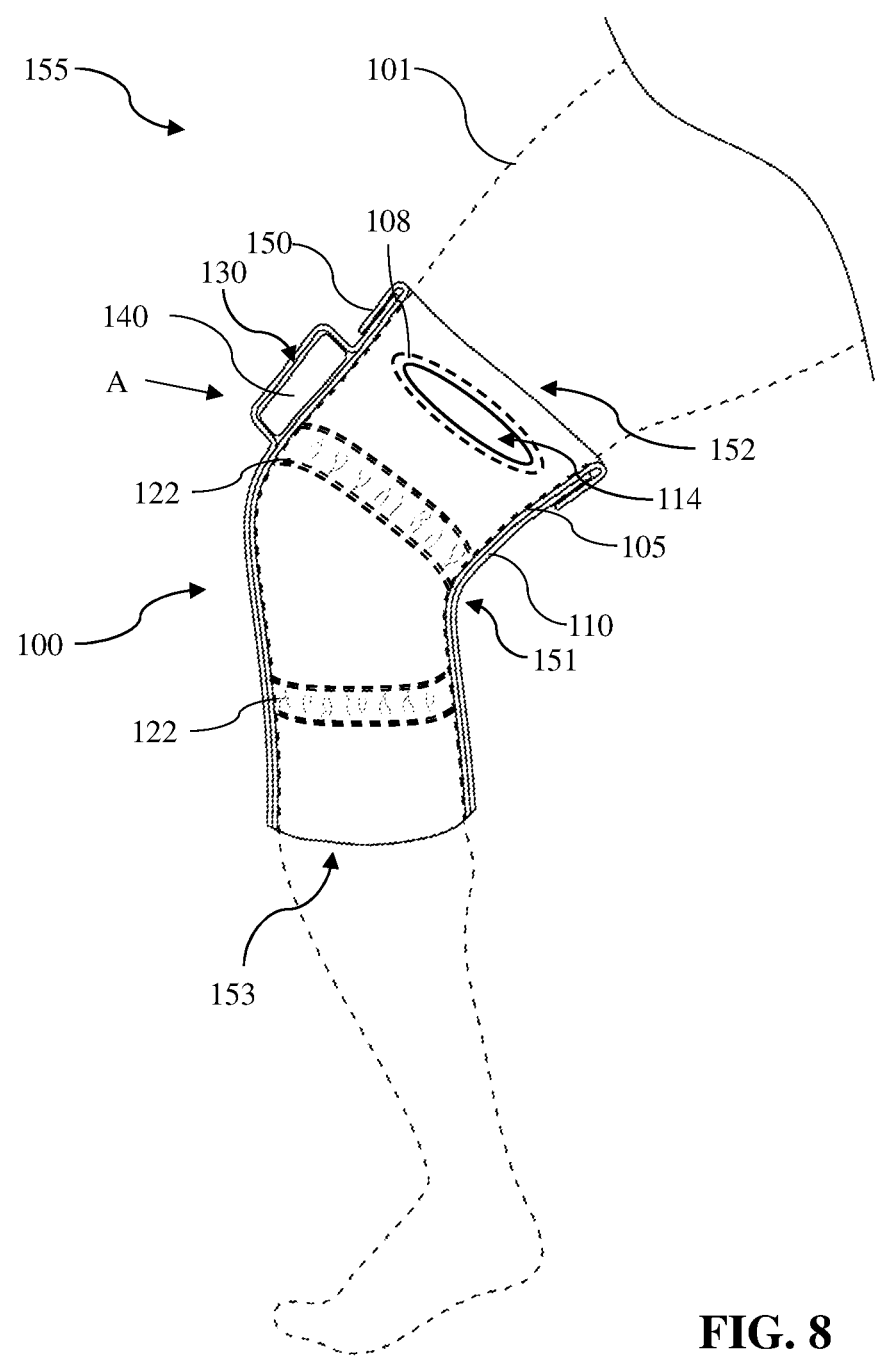
FIG. 8 is a side cross-sectional view of a system of an apparatus for at least one of icing, heating and compressing a user's body part, according to an example embodiment.

FIGS. 7-8 illustrate a system 155 for at least one of icing, heating, and compressing a user's body part 101 and will be discussed together for ease of reference. The system 155 includes a wearable device 100, and at least one of a hot element and a cold element positioned within a compartment on the wearable device. The wearable device 100 comprises an inner part 105 and outer part 110. The outer part 110 is arranged with the inner part 105 such that the outer part surrounds the inner part. The inner part 105 includes an inner part upper end 106 and an inner part lower end 107, defining an inner part length. The inner part provides a protective insulation layer between a cold or heat modality and a user's skin. The inner part 105 is arranged having a first set of elastic properties and a first tubular shape such that the inner part 105 is configured to fit snugly around a user's body part. The outer part 110 includes an outer part upper end 111 and an outer part lower end 112 defining an outer part length. The outer part may be comprised of a water-wicking material to draw moisture away from the body and prevent ice from leaking during treatment. However, it is understood that other types of materials may be used and are within the spirit and scope of the present invention. The outer part 110 has a second set of elastic properties, also configured to fit snugly around a user's body part, and a second tubular shape. The system includes a first set of elastic properties defining a first resilient force of between 17 mmHg-22 mmHg, and as described more fully below, when the wearable device 100 is in a fully sealed configuration, the second set of elastic properties defines a second resilient force of between 17 mmHg-22 mmHg.

In another embodiment, the wearable device is a knee sleeve comprising a main body member 151. The main body member is generally tubular for encircling the knee region of the user 101. The upper end of the main body member has a first opening 152 to accommodate the upper knee region of the user. The first opening is defined by a flap 150 forming a seal at the upper end of the wearable device 100. The flap is defined by the inner part length being greater than the outer part length such that the inner part upper end 106 folds over the outer part upper end 111. When the wearable device 100 is in a fully sealed configuration, the flap 150 extends at least 1.0 inch from a top edge of the upper end of the outer part. The lower end of the main body member has a second opening 153 to accommodate the lower knee region of the user. The first and second openings are appropriately sized and positioned so that the leg of the user may comfortably extend through the first and second opening of the main body member.

The wearable device may be comprised of different flexible materials such as Lycra, polyester, cotton blend, nylon, similar blends, or any other suitable materials known in the art. More specifically, and without limitation, the material can be moisture absorbent, breathable, stretchable, meshed, or any blend or combination thereof. The material can also be thermoconductive to conduct heat better, or thermoreflective to help keep heat inside the wearable device. Further, the thickness and elasticity of fabric may be varied to accommodate different users and conditions. It should be appreciated that the wearable device can have other shapes and dimensions to accommodate men, women, and children of all sizes, and such variations are within the spirit and scope of the claimed invention.

The wearable device further includes a first attaching means 120 for attaching the inner part lower end 107 to the outer part lower end 112. The first attaching means is configured such that the therapeutic modality does not move below the lower ends. The first attaching means may include a strap, button, pocket, hook and loop fastener, ridge, etc. In the present embodiment, the first attaching means 120 comprises stitching the inner part lower end 107 to the outer part lower end 112 such that the outer part surrounds the inner part. A plurality of different stitch patterns can be used including a chain stitch, straight stitch, and zigzag stitch, and such variations are within the spirit and scope of the claimed invention. Additionally, the stitching thread can be comprised of a natural fiber (cotton, wool, silk, linen) or a synthetic fiber (rayon, polyester, nylon). It should also be appreciated that other attachment means can be used to attach the inner part lower end 107 to the outer part lower end 112, including fasteners, snaps, zippers, ties, or any other suitable method known in the art.

The wearable device further includes a compartment 130 defined by the space between the outer part 110 and the inner part 105, located above the first attaching means 120 and positioned outward from the user's body. The space may vary in size across other embodiments. The compartment is configured for receiving at least one of a hot element and cold element 140. As best shown in FIG. 6, when the wearable device 100 is not in a fully sealed configuration, the therapeutic modality may be easily positioned directly over any injured area and adjusted without removing, changing or adding layers within the compartment in an unlimited number of positions within the compartment spanning the entire wearable device.

A compression force is provided by the second set of elastic properties compressing at least one of a hot element and cold element against the user's body part 101. The hot and cold elements may be comprised of crushed ice, commercially available ice and gel packs, hot water bottles, heat pads, and heated stones. The compression force provides an inward force (in the direction of line A) of at least 17 mmHg against the user's body part, thereby eliminating a second attaching means above the first attaching means 120. As mentioned, above, the second attaching means being a structure other than the outer part 110 for securing the at least one of the hot element and cold element against the user's body part 101, and may include a strap, button, pocket, hook and look fastener, snap, ridge or any combination thereof. FIG. 8 illustrates that the wearable device snugly fits the body of the user 101 such that a therapeutic modality located inside the compartment is anchored precisely over the knee area due to the snug fit of the wearable device. By eliminating a second attaching means above the first attaching means, the wearable device can be worn as any layer of clothing, including as an undergarment or as an over-garment, and permits the user to move, in moderation, without disturbing the precision of treatment. Additionally, the compression force provided by the second set of properties is configured such that the second attaching means is eliminated thereby allowing the user to position the hot element or cold element in a much greater amount of locations more easily that the existing prior art. Additionally as mentioned above the inner part may also provide an amount of friction thereby facilitating prevention of movement of the hot element or cold element when the element is positioned within the compartment and the wearable device is worn by the user.

Figure 9:
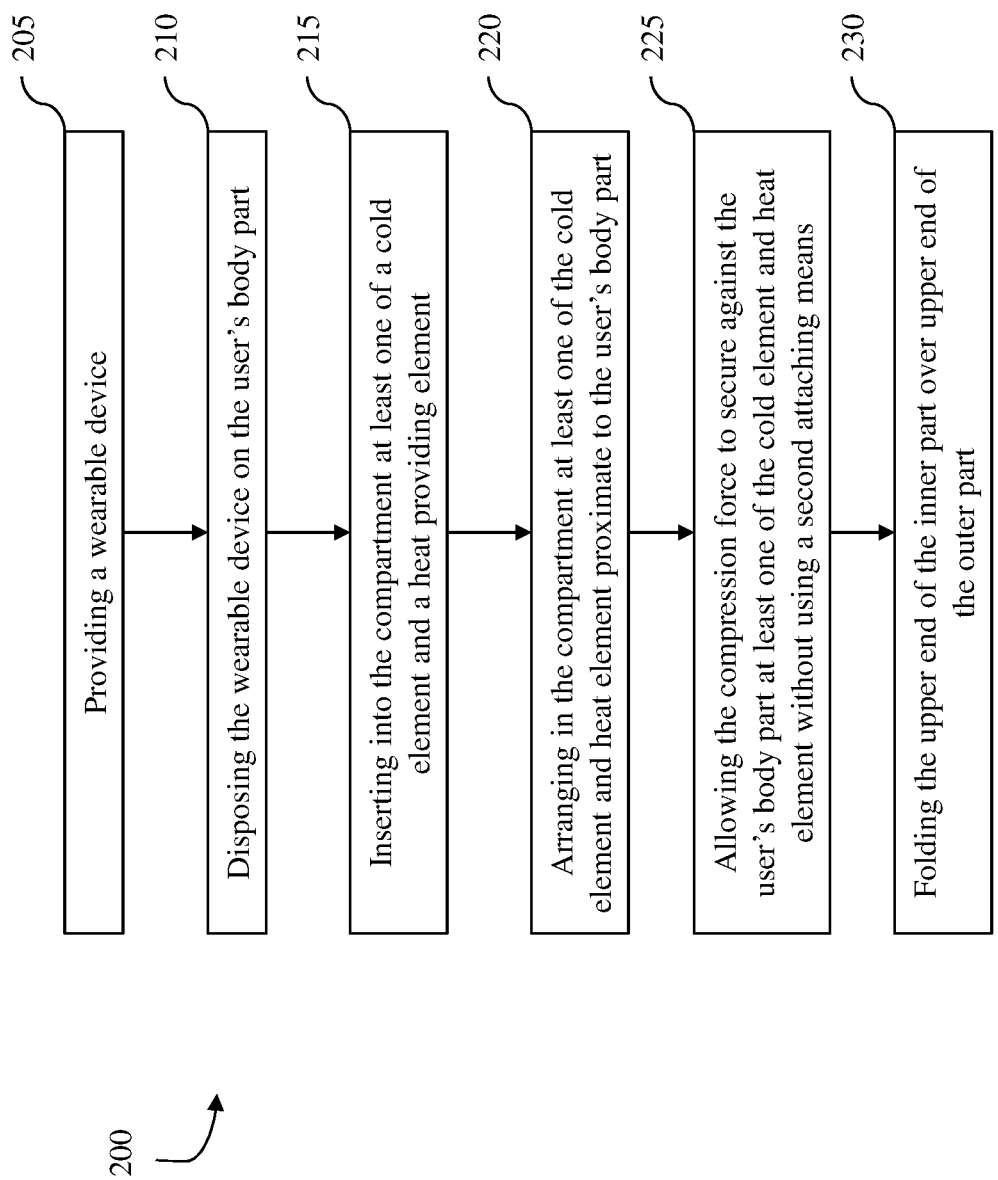
FIG. 9 is a flowchart illustrating the steps for a method for at least one of icing, heating, and compressing a user's body part, according to an example embodiment.

FIG. 9 is a flowchart describing the steps of the method for at least one of icing, heating, and compressing a user's body part, according to an example embodiment of the present invention. The sequence of steps depicted is for illustrative purposes only and is not meant to limit the method in any way as it is understood that the steps may proceed in a different logical order, additional or intervening steps may be included, or described steps may be divided into multiple steps, without detracting from the invention.

The method 200 begins with step 205, providing a wearable device. As described above, with respect to FIGS. 2-8, the wearable device 100 comprises an inner part 105 and outer part 110. The outer part 110 is arranged with the inner part 105 such that the outer part surrounds the inner part. The inner part 105 includes an inner part upper end 106 and an inner part lower end 107, defining an inner part length. The inner part provides a protective insulation layer between a cold or heat modality and a user's skin. The inner part 105 has a first set of elastic properties and a first tubular shape such that the inner part 105 is configured to fit snugly around a user's body part. The outer part 110 includes an outer part upper end 111 and an outer part lower end 112 defining an outer part length. The outer part may be comprised of a water-wicking material to draw moisture away from the body and prevent ice from leaking during treatment. The outer part 110 has a second set of elastic properties and a second tubular shape. The first set of elastic properties defines a first resilient force of between 17 mmHg-22 mmHg, and as described more fully below, when the wearable device 100 is in a fully sealed configuration, the second set of elastic properties defines a second resilient force of between 17 mmHg-22 mmHg. It is important that the second resilient force be sufficient such that the compression force or inward force provided by the second set of elastic properties is sufficient such that the hot element and cold element is maintained where it is positioned and such that the need for the second attaching means, being structure, is eliminated. A flap is defined by the inner part length being greater than the outer part length such that the inner part upper end 106 folds over the outer part upper end 111. When the wearable device 100 is in a fully sealed configuration, the flap 150 extends at least 1.0 inch from a top edge of the upper end of the outer part. The wearable device further includes a first attaching means 120 arranged for attaching the inner part lower end 107 to the outer part lower end 112 such that the outer part surrounds the inner part. The first attaching means is configured such that the therapeutic modality does not move below the lower ends. A compartment 130 is defined by the space between the outer part 110 and the inner part 105, located above the first attaching means 120. The compartment is configured for receiving at least one of a hot element and cold element 140. A compression force is provided by the second set of elastic properties compressing at least one of a hot element and cold element against the user's body part 101. As shown in FIGS. 3-5, the compression force provides an inward force (in the direction of line A) of at least 17 mmHg against the user's body part, thereby eliminating a second attaching means above the first attaching means 120. A first handle opening and a second handle opening extends through the outer part and the inner part located opposing sides. The first handle opening and the second handle opening are disposed on opposing sides of the wearable device. For example, when the wearable device is worn, the first handle opening may be on the right side of the user's body part, and the second handle opening may be on the left side of the ser's body part. The wearable device may include additional handle openings, not located on opposing sides, to pull up different parts of the wearable device. The wearable device also includes at least one band 122 having a third set of elastic properties that is greater than the first set of elastic properties of the inner part and the second set of elastic properties of the outer part.

The band may be positioned so that it is outside the inner surface of the outer part so that the band does not unnecessarily obstruct the compartment. In other words, the band is such that it provides a compressive force without adding elements within the compartment (which is between the inner surface of the outer layer and the outer surface of the inner layer). The band may be of an elastic material and other types of materials may be used and are within the spirit and scope of the present invention.

In step 210, the method includes disposing the wearable device on the user's body part. Disposing the wearable device includes pulling the wearable device onto the user's body part, ideally using the first handle opening and the second handle opening disposed on opposing sides. The user's body is positioned inward from a channel from the inner part, and the compartment is positioned outward from the user's body part. The at least one band 122 is disposed proximate to a target area of the user. The target area of the user may be the portion of the user's body part that may need more compression. The target area of the user may also be the portion where the user requires the hot element or the cold element such that the band is disposed directly below the compartment containing the hot element or the cold element. The band provides more compression to prevent the hot element or cold element, one inserted into the compartment, from sliding down between the inner part and outer part where the band is disposed. The band may be stitched to the inner side of the outer part. In one embodiment may be a looped element or continuous looped shaped elastic band that is sticked to the inward facing surface of the outer part so that the band provides a compressive force on a user's body.

As shown in FIGS. 2-6, in one embodiment, the wearable device is a pair of shorts comprising a main body member 116 and a pair of leg sections 117 (a), 117 (b). The main body member is generally tubular for encircling the hip region of a user. The upper end of the main body member has an opening 118 to accommodate the hip region of a user. The lower end of the main body member has a pair of openings 119 (a), 119 (b) to accommodate the legs of the user and are appropriately sized and positioned so that the legs of the user may comfortably extend through the main body member.

As shown in FIGS. 7-8, in another embodiment, the system includes a wearable device being a knee sleeve comprising a main body member 151. The main body member is generally tubular for encircling the knee region of the user 101. The upper end of the main body member has a first opening 152 to accommodate the upper knee region of the user. The lower end of the main body member has a second opening 153 to accommodate the lower knee region of the user. The first and second openings are appropriately sized and positioned so that the leg of the user may comfortably extend through the first and second opening of the main body member.

Figure 11:
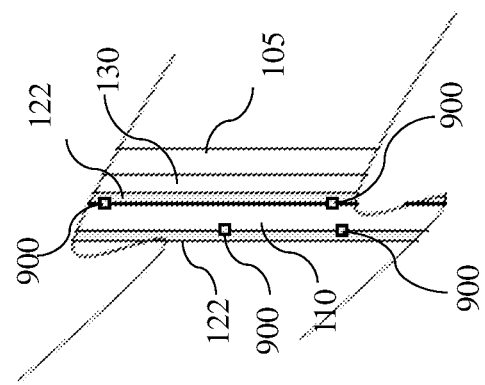
FIG. 11 is a partial cross-sectional view of a pair of bands attached to the outer part; according to an example embodiment.
Figure 10:
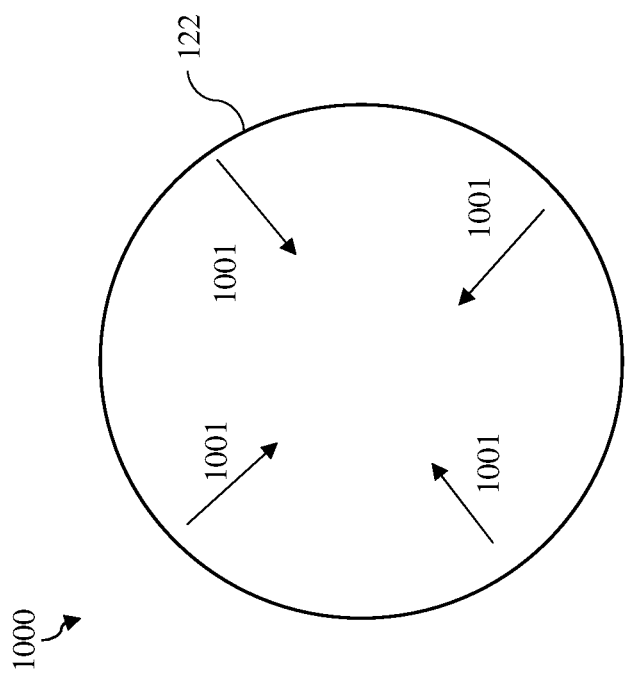
FIG. 10 is a top view of a diagram of a band, according to an example embodiment.

Referring to FIGS. 10 and 11, FIG. 10 is a top view of a diagram of a band, according to an example embodiment and FIG. 11 is a partial cross-sectional view of a pair of bands (122) attached to the outer part 110. The band is looped to wrap around the body part when the wearable device is worn. In one embodiment, the band may be attached by stitching 900 to the inward facing side of the outer part so that hot and cold elements can easily be positioned inward from the band inside the compartment 130. The thickness of the band is configured to be thin enough to not obstruct the compartments. The band should not obstruct the compartment because the user may decide to push the hot element or cold element further below the band. Additionally, a second band (122) may be attached to the wearable device by stitching 900 to the surrounding outward facing part of the outer part so that hot and cold elements inserted can easily be positioned inward from the band inside the compartment 130. In other embodiments, the bands may be attached to the outer part via other processes. The thickness of the second band is also configured to be thin enough such the second band may be seamlessly disposed on the wearable device. As mentioned above and shown in FIG. 10, the bands 1000 apply a compressive force in the direction of arrowed lines 1001 such that when the bands are on a user's body the compressive force prevents cold and hot elements from moving downward and falling out of position. Because the bands have the third set of elastic properties that are tighter than the elastic properties of the outer part and inner part, the compressive force of the bands tightens the area of the wearable device more where the bands are positioned. Therefore, the bands push the outer part against the inner part to tighten the gap between the inner part and the outer part. While the wearable device is worn, the tightened gap prevents the inserted hot element or cold element from moving below the area of the wearable device where the bands are positioned. The increased compression may also provide more stabilization to the user's muscles where the bands are positioned. In other embodiments, the band may be a looped drawstring disposed on the outward facing part of the outer part. The drawstring would provide the same compressive force in the direction of the arrowed lines 1001 configured to tighten the gap between the outer part and the inner part. Additionally, the band may have a height (top of band to bottom of ban) substantially less than the length (from the upper end to the lower end) of the outer part and inner part as illustrated in the figures.

Figure 12:
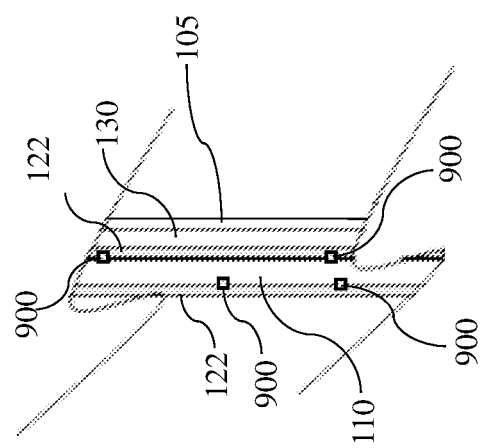
FIG. 12 is a partial cross-sectional view of more clearly illustrating the widths of the outer part and inner part, according to an example embodiment.

FIG. 12 further illustrates that the thickness of the outer part 110 has an outer part thickness that is greater than the thickness of the inner part. Inner part may be a thickness of 200 grams per square meter (GSM), which is lighter and thinner weight than the outer part, which may allow for easy on application, allow for smooth sliding surface to receive ice, and frostbite insulation protection when the device is worn by the user. The outer part 110 may have comprise 250 grams per square meter (GSM), which is heavier or thicker material than the inner part 105 for clamping capability to hold ice in place against a user in unlimited positions throughout the sleeve (capacity, region, etc). However, other ranges may be used and are within the spirit and scope of the present invention as long as the outer part 110 has a greater weight or thickness and provide a greater compression force when the device is worn by the user than the inner part 105. Each sleeve may comprise of at least Nylon which produces a stronger, less stretchy material. It is understood that thickness may also be used to refer to the weight of fabric. In short, the weight of the fabric on the outer part may be greater than the weight of the fabric of the inner part.

In step 215, the method includes inserting into the compartment at least one of a cold element and a heat providing element. The hot and cold elements may be comprised of crushed ice, commercially available ice and gel packs, hot water bottles, heat pads, and heated stones. As best shown in FIG. 6, when the wearable device 100 is not in a fully sealed configuration, the at least one of the cold element and heat element may be positioned and adjusted without removing, changing or adding layers within the compartment in an unlimited number of positions within the compartment spanning the entire wearable device. Additionally, the present embodiment allows the user to insert and position a hot element or cold element proximate to a user's body and within the wearable device in numerous positions without being limited by use of a fastener such as a hook, button, flap, snap, ridge, etc.

In step 220, the method includes arranging in the compartment at least one of the cold element and heat element proximate to the user's body part. For example, in FIG. 3, a cold element 140 is positioned over the lower back (lumbar muscle) of the user 101, and in FIG. 4, one cold element positioned over the anterior wall (abdominal muscle) of the user 101. In FIG. 5, three cold elements are simultaneously positioned over the lower back (lumbar muscle), the anterior wall (abdominal muscle), and posterior pelvic region (gluteus maximus muscle) of the user 101. Force (opposing the inward force in the direction of line A) may be applied to the outer part to stretch the outer part and enlarge the compartment so that the hot element or cold element may be positioned into the compartment. After positioning the hot element or cold element into the compartment, then the force stretching the outer part to enlarge the compartment may be removed so that the compression force provided by the outer layer compresses the hot element or cold element against the user's body.

In step 225, the method includes allowing the compression force to secure against the user's body part at least one of the cold element and heat element without using a second attaching means. The heat element and/or cold element are unrestrictedly positioned above the first attaching means such that the heat element and cold element are removably positioned within the compartment. The heat element and/or cold element may be removed from the compartment by the user. This allows the user to replace or flip the heat element and/or cold element. The second attaching means is a structure other than the outer part 110 for securing the at least one of the hot element and cold element against the user's body part 101, and may include a strap, button, pocket, hook and look fastener, snap, ridge or any combination thereof. As shown in FIGS. 3-5, the compression force provides an inward force (in the direction of line A) of at least 17 mmHg against the user's body part, thereby eliminating a second attaching means above the first attaching means 120. By eliminating a second attaching means above the first attaching means, the wearable device can be worn as any layer of clothing, including as an undergarment or as an over-garment, and permits the user to move, in moderation, without disturbing the precision of treatment. Additionally, by eliminating the second attaching means allows the user to position the hot element or cold element in a much greater amount of locations more easily that the existing prior art.

In step 230, the method includes folding the upper end of the inner part over the upper end of the outer part so that the flap is positioned outward from the outer part creating the seal. As discussed above, the flap is defined by the inner part length being greater than the outer part length such that the inner part upper end 106 folds over the outer part upper end 111. Thus, when the wearable device 100 is in a fully sealed configuration, the flap 150 extends at least 1.0 inch from a top edge of the upper end of the outer part.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A wearable device for at least one of icing, heating and compressing a user's body part, the wearable device comprising:
    an inner part having an inner part upper end and an inner part lower end defining an inner part length, wherein the inner part has a first set of elastic properties and a first tubular shape such that the inner part is configured to fit snugly around a user's body part, and wherein the inner part has an inner part thickness;
    an outer part having an outer part upper end and an outer part lower end defining an outer part length, wherein the outer part has a second set of elastic properties and a second tubular shape, wherein the outer part is arranged with the inner part such that the outer part surrounds the inner part, and wherein the outer part has an outer part thickness that is greater than the inner part thickness;
    a first attaching means for attaching the inner part lower end to the outer part lower end;
    compartment is defined by a space between the outer part and the inner part and above the first attaching means; and
    a compression force provided by the second set of elastic properties compressing at least one of a hot element and a cold element against the user's body part thereby eliminating a second attaching means above the first attaching means within the compartment, wherein the second attaching means being structure other than the outer part for securing the at least one of the hot element and cold element against the user's body part.

2. The wearable device of claim 1, wherein at least one handle is in attachment with the outer part.

3. The wearable device of claim 2, wherein the at least one handle is defined by a first handle opening extending through the outer part and the inner part.

4. The wearable device of claim 1 comprising at least one band disposed on the outer part between the outer part upper end and outer part lower end, the band having a third set of elastic properties that is greater than the first set of elastic properties and the second set of elastic properties.

5. The wearable device of claim 1, wherein the first set of elastic properties defines a first resilient force of between 17 mmHg-22 mmHg and the second set of elastic properties defines a second resilient force of between 17 mmHg-22 mmHg.

6. The wearable device of claim 1, wherein the compression force is providing an inward force of at least 17 mmHg against the user's body part.

7. The wearable device of claim 1, wherein the first attaching means comprises stitching attaching the inner part lower end to the outer part lower end.

8. The wearable device of claim 1, wherein the second attaching means comprises a strap, button, pocket, hook and loop fastener, snap, ridge or any combination thereof.

9. A system for at least one of icing, heating and compressing a user's body part, the system comprising:
    a wearable device having;
        an inner part having an inner part upper end and an inner part lower end defining an inner part length, wherein the inner part has a first set of elastic properties and a first tubular shape such that the inner part is configured to fit snugly around a user's body part, and wherein the inner part has an inner part thickness;
        an outer part having an outer part upper end and an outer part lower end defining an outer part length, wherein the outer part has a second set of elastic properties and a second tubular shape, wherein the outer part is arranged with the inner part such that the outer part surrounds the inner part, and wherein the outer part has an outer part thickness that is greater than the inner part thickness;
a first attaching means for attaching the inner part lower end to the outer part lower end;
a compartment for receiving at least one of a hot element and a cold element, wherein the compartment is defined by a space between the outer part and the inner part and above the first attaching means;
a compression force provided by the second set of elastic properties compressing at least one of the hot element and the cold element against the user's body part thereby eliminating a second attaching means above the first attaching means;
wherein the second attaching means being structure other than the outer part for securing at least one of the hot element and the cold element against the user's body part;
a first handle opening and a second handle opening extending through the outer part and the inner part, wherein the first handle opening and the second handle opening are disposed on opposing sides of the wearable device; and
at least one of the hot element and the cold element positioned within the compartment.

10. The system of claim 9, comprising at least one of a band having a third set of elastic properties that is greater than the first set of elastic properties of the inner part and the second set of elastic properties of the outer part.

11. The system of claim 9, wherein the first set of elastic properties defines a first resilient force between 17 mmHg-22 mmHg.

12. The system of claim 9, wherein the second set of elastic properties defines a second resilient force between 17 mmHg-22 mmHg.

13. The system of claim 9, wherein the compression force is providing an inward force at least 17 mmHg against the user's body part.

14. The system of claim 9, wherein the first attaching means comprises stitching attaching the inner part lower end to the outer part lower end.

15. The system of claim 9, wherein the second attaching means comprises a strap, button, pocket, hook and loop fastener, snap, ridge or any combination thereof.

16. A method for at least one of icing, heating and compressing a user's body part, the method comprising:
a) providing a wearable device, wherein the device comprises,
    an inner part having an inner part upper end and an inner part lower end defining an inner part length, wherein the inner part has a first set of elastic properties and a first tubular shape such that the inner part is configured to fit snugly around a user's body part, and wherein the inner part has an inner part thickness;
    an outer part having an outer part upper end and an outer part lower end defining an outer part length, wherein the outer part has a second set of elastic properties and a second tubular shape, wherein the outer part is arranged with the inner part such that the outer part surrounds the inner part;
    a first attaching means for attaching the inner part lower end to the outer part lower end;
    a compartment for receiving ice defined by a space between the outer part and the inner part and above the first attaching means;
    a compression force provided by the second set of elastic properties compressing at least one of a heat element and a cold element against the user's body part thereby eliminating a second attaching means above the first attaching means, wherein the second attaching means being structure other than the outer part for securing the at least one of the heat element and the cold element against the user's body part;
    a first handle opening and a second handle opening extending through the outer part and the inner part, wherein the first handle opening and the second handle opening are disposed on opposing sides of the wearable device; and
    at least one of a band having a third set of elastic properties that is greater than the first set of elastic properties of the inner part and the second set of elastic properties of the outer part;
b) pulling the wearable device onto the user's body part using the first handle opening and the second handle opening;
c) disposing of the wearable device on the user's body part, wherein the user's body is positioned inward from a channel from the inner part and wherein the compartment is positioned outward from the user's body part and wherein the band is disposed proximate to a target area of the user;
d) inserting into the compartment above the band at least one of the cold element and the heat element;
e) arranging in the compartment at least one of the cold element and the heat element proximate to the user's body part; and
f) allowing the compression force to secure against the user's body part at least one of the cold element and the heat element without using a second attaching means.

17. The method of claim 16, wherein compression force provided by the second set of elastic properties allows at least one of the cold element and the heat element to be positioned in the compartment unrestrictedly above the first attaching means.

18. The method of claim 16, wherein the second set of elastic properties defines a second resilient force between 17 mmHg-22 mmHg.

19. The method of claim 16, wherein the compression force is providing an inward force at least between 17 mmHg against the user's body part.

20. The method of claim 16, wherein the second attaching means comprises a strap, button, pocket, hook and loop fastener, snap, ridge or any combination thereof.

* * * * *